United States Patent
Grashow

(10) Patent No.: US 10,092,477 B2
(45) Date of Patent: Oct. 9, 2018

(54) USE OF SECONDARY METRICS IN NECK SUCTION THERAPY

(71) Applicant: KONINKLIJKE PHILIPS N.V., Eindhoven (NL)

(72) Inventor: Jonathan Sayer Grashow, Cheswick, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 860 days.

(21) Appl. No.: 14/403,584

(22) PCT Filed: May 17, 2013

(86) PCT No.: PCT/IB2013/054047
§ 371 (c)(1),
(2) Date: Nov. 25, 2014

(87) PCT Pub. No.: WO2013/179176
PCT Pub. Date: Dec. 5, 2013

(65) Prior Publication Data
US 2015/0173997 A1    Jun. 25, 2015

Related U.S. Application Data

(60) Provisional application No. 61/654,109, filed on Jun. 1, 2012.

(51) Int. Cl.
*A61H 7/00* (2006.01)
*A61F 5/56* (2006.01)

(52) U.S. Cl.
CPC .............. *A61H 7/00* (2013.01); *A61F 5/56* (2013.01); *A61H 2201/5064* (2013.01); *A61H 2201/5092* (2013.01); *A61H 2205/04* (2013.01)

(58) Field of Classification Search
CPC .............. A61H 7/00; A61H 2205/04; A61H 2201/5064; A61H 2201/5092; A61F 5/56
See application file for complete search history.

(56) References Cited

U.S. PATENT DOCUMENTS

| 5,343,878 A | 9/1994 | Scarberry | |
| 6,935,335 B1 * | 8/2005 | Lehrman | A61B 5/0002 128/200.24 |
| 7,182,082 B2 | 2/2007 | Hoffrichter | |
| 2008/0163875 A1 * | 7/2008 | Aarestad | A61F 5/56 128/848 |

(Continued)

FOREIGN PATENT DOCUMENTS

| DE | 20111396 U1 | 10/2001 |
| WO | WO2008076421 A2 | 6/2008 |

*Primary Examiner* — Quang D Thanh
(74) *Attorney, Agent, or Firm* — Michael W. Haas

(57) ABSTRACT

Provided are systems (100) for control of or determining the effectiveness of a neck suction device using one or more secondary metrics. A sensor device (101) may be used to measure or determine one or more secondary metrics relating to the neck of a patient in response to the application of suction to the neck of the patient proximal to the hyoid bone of the patient by a neck suction device. A processing device (107) may then determine whether to adjust the suction intensity in response to the measured/determined metrics. The metrics may also be use do determine whether neck suction is likely to be effective for a specific patient.

10 Claims, 9 Drawing Sheets

(56) References Cited

U.S. PATENT DOCUMENTS

2009/0177124 A1   7/2009  Silwa
2011/0066086 A1*  3/2011  Aarestad .................. A61F 5/56
                                                  601/11
2014/0046184 A1*  2/2014  Heinrich ............. A61B 5/0064
                                                  600/438

* cited by examiner

USE OF SECONDARY METRICS IN NECK SUCTION THERAPY

CROSS-REFERENCE TO RELATED APPLICATIONS

This patent application claims the priority benefit under 35 U.S.C. § 371 of international patent application no. PCT/IB2013/054047, filed May 17, 2013, which claims the priority benefit under 35 U.S.C. § 119(e) of U.S. Provisional Application No. 61/654,109 filed on Jun. 1, 2012, the contents of which are herein incorporated by reference.

BACKGROUND OF THE INVENTION

1. Field of the Invention

The present disclosure pertains to systems and methods for the use of secondary metrics for control and effectiveness evaluation of neck suction devices.

2. Description of the Related Art

In some instances, treatment of obstructive sleep apnea (OSA) may be accomplished using a device affixed to the frontal portion of the neck, such that the airway may be opened by the application of a negative pressure (suction). The typical control scheme for such treatment is based on measurement of the vacuum or vacuum force that is applied to the neck, as a primary metric in controlling the vacuum generating device. The primary disadvantage of this method is that it does not include a direct measure of the effectiveness of the applied pressure to open the airway. Accordingly, improved control schemes for neck suction administration may be desirable.

An additional problem with the application of current devices is that the method of applying a vacuum to the neck effectively opens the airway of some patients, but is ineffective in others. It has been posited that this is due to differences in anatomical geometries and mechanical properties of neck tissues. Accordingly, effective evaluation of patient receptiveness to neck suction may also be desirable.

SUMMARY OF THE INVENTION

It is an object of one or more embodiments described herein to provide a system for providing neck suction therapy that includes a neck suction device configured to apply suction to an area on a neck of a patient proximal to a hyoid bone of the patient. A sensor portion is configured to measure a characteristic of the area on the neck of the patient during application of suction by the neck suction device. A processing device is configured to receive information regarding the measured characteristic. The suction intensity of the neck suction device is adjusted using the information regarding the measured characteristic.

It is yet another aspect of one or more embodiments of the present invention to provide a method for providing neck suction therapy that includes (a) applying suction to an area on a neck of a patient proximal to a hyoid bone of the patient using a neck suction device; (b) measuring a characteristic of the area on the neck of the patient during application of suction by the neck suction device; and (c) adjusting a suction intensity of the neck suction device using information regarding the measured characteristic.

It is yet another aspect of one or more embodiments to provide a system for controlling a neck suction device, comprising: treatment means for applying suction to an area on a neck of a patient proximal to a hyoid bone of the patient; sensor means for measuring a characteristic of the area on the neck of the patient during application of suction by the neck suction device; and processor means for: receiving information regarding the measured characteristic, and adjusting a suction intensity of the neck suction device using the information regarding the measured characteristic.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention

DETAILED DESCRIPTION OF EXEMPLARY EMBODIMENTS

Figure 1:
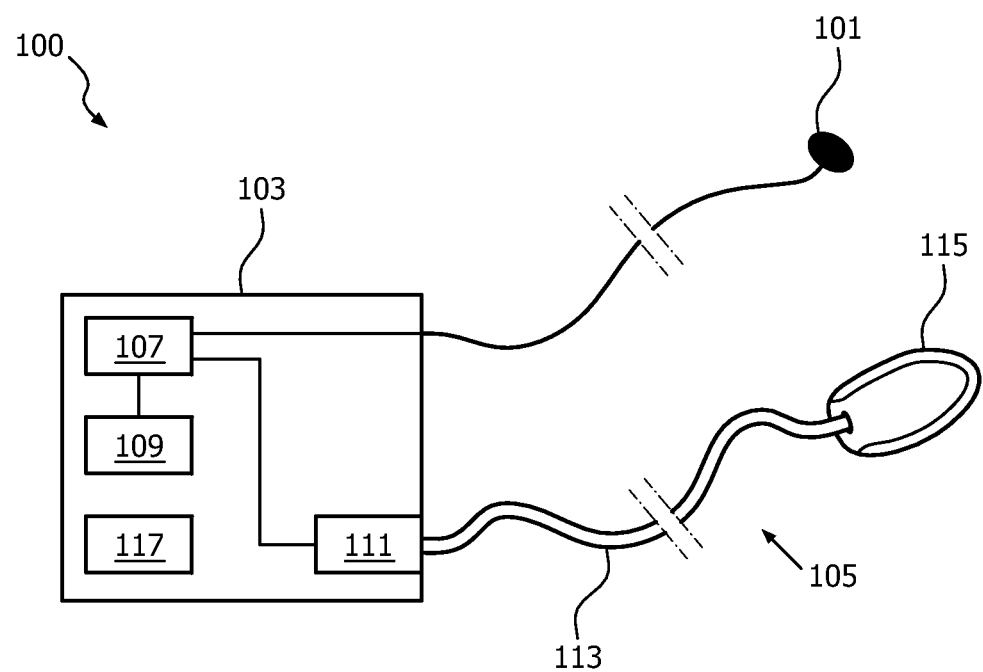
FIG. 1 is an example of a system for control of neck suction using secondary metrics, according to various embodiments of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The improved control of neck suction delivery provided herein may utilize one or more secondary metrics that are better indicators of the effectiveness of the applied pressure than generated suction intensity. For example, a hyoid force metric (i.e., the force applied to the hyoid bone by the generated neck suction) inherently accounts for variations in neck geometry or other patient anatomy as well as variations in the alignment of a patient interface of a treatment device. Such measurements are not taken into account when suction intensity alone is monitored.

Another example metric, hyoid displacement (i.e., the displacement of the hyoid bone effected by applied suction) provides a direct measurement of the effect of the applied vacuum as opposed to measurements of treatment dosage (e.g., suction intensity or force). By measuring displacement, it is possible to more accurately account for variations in the mechanical properties of the patient's throat and surrounding tissues as well as external forces (e.g. gravity) that may act differently on the neck tissues depending on variable factors (e.g. orientation: lying down or standing up).

Accordingly, systems and methods for controlling a neck suction device using secondary metrics are provided herein. In some embodiments, the use of measurements relating to forces applied to a neck by a neck suction device and/or the use of measurements relating to displacement in certain areas of the neck (e.g., the hyoid bone) may be used to adjust the intensity of a neck suction device that provides treatment to a patient.

FIG. 1 illustrates a system 100, which is an example of a system for using secondary metrics to control a neck suction device. In some embodiments, system 100 may include a sensor portion 101, a control portion 103, a treatment portion 105, and/or other portions.

Sensor portion 101 may include a sensor that may be used to measure one or more secondary metrics or other characteristics of a patient that can be used to control delivery of treatment to the patient. For example, in some embodiments, sensor portion 101 may be a force measurement device that is configured to measure or determine a force applied to a portion of a patient's anatomy by treatment portion 105.

Figure 2A:
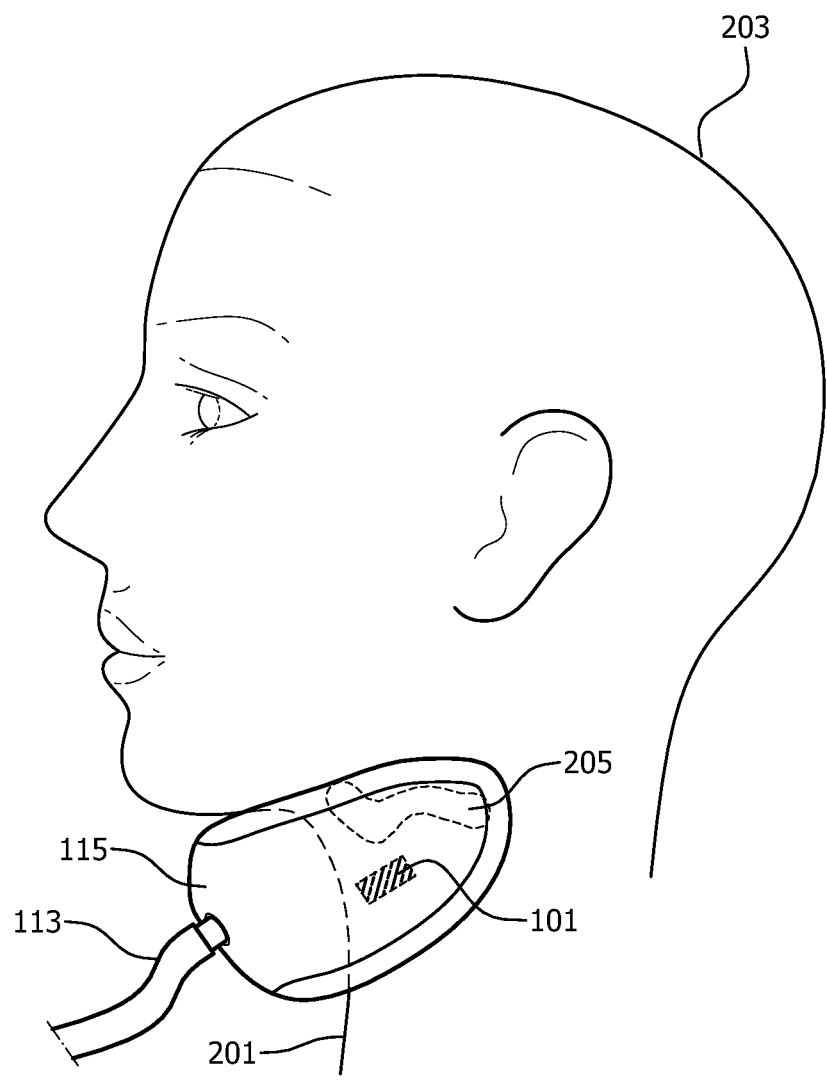
FIGS. 2A and 2B illustrate examples of placement of a treatment portion and a sensor portion on a patient, according to various embodiments of the invention.
Figure 2B:
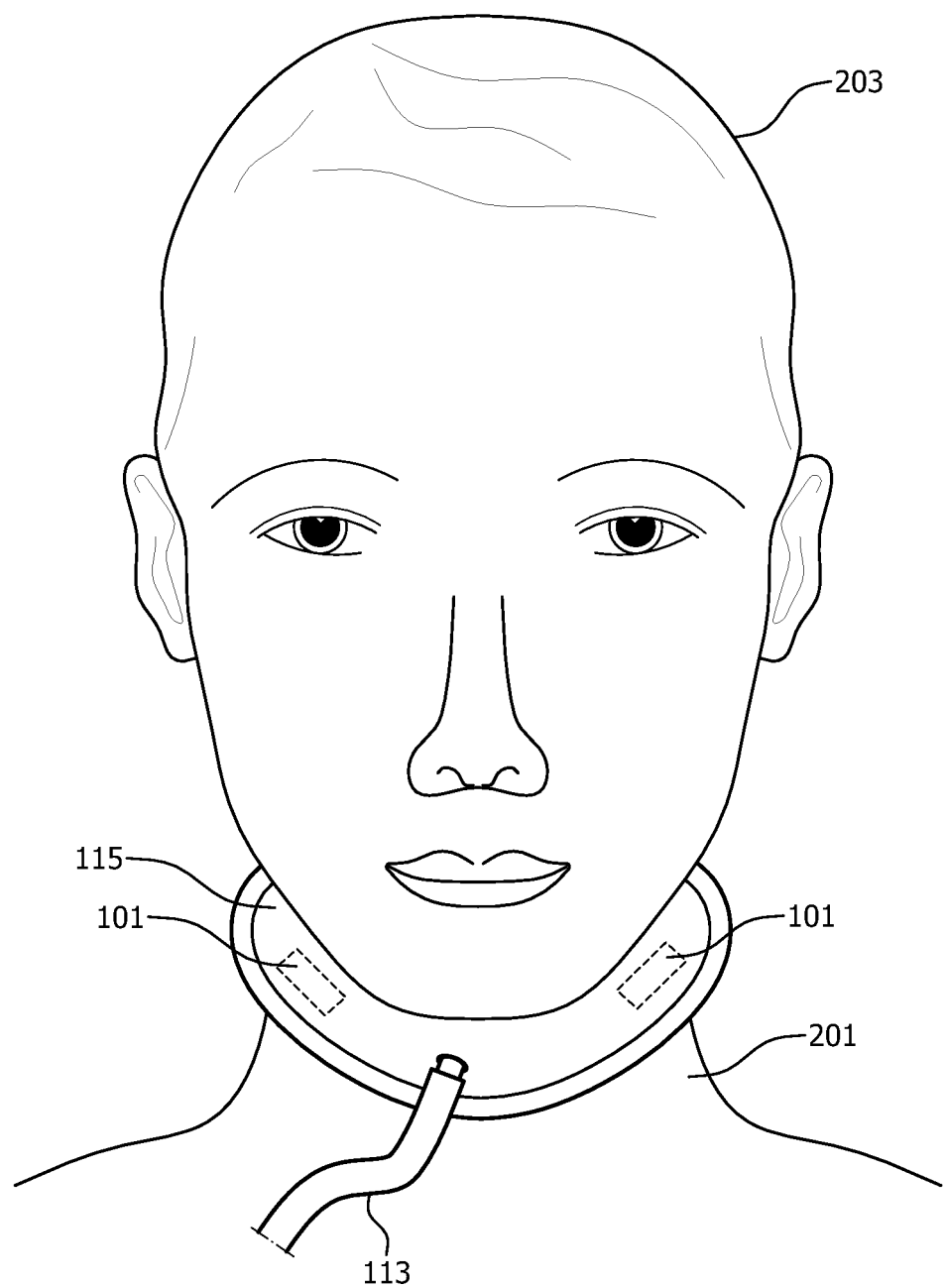

In some embodiments, the portion of the patient's anatomy where the force measurement is made or determined is the hyoid bone of the patient. For example, measurement of force to the hyoid bone may be accomplished by attaching a force measurement device to a neck suction therapy device (e.g., a patient interface 115 of treatment portion 105) so as to measure the force applied by the neck suction device. In some embodiments, the force applied to the hyoid bone may be derived using the measurement of this force provided to the patient's neck by the neck suction device. FIGS. 2A and 2B illustrate sensor portion 101 attached to patient interface 115 of treatment portion 105 (e.g., a neck suction device) proximal to the neck 201 of patient 203.

A force measurement device that may be used as sensor portion 101 may include a strain gauge that is mounted on a neck suction device. For example, in some embodiments, a patient interface 115 may include a suction bladder therein to which a strain gauge may be mounted so as to monitor force variation applied to the neck of the patient. In some embodiments, a strain gauge or other force measurement sensor may be attached to a support wall of a patient interface 115 so as to measure the force applied by treatment portion 105.

In some embodiments, the force applied to the neck of the patient by the neck suction device may be used with displacement measurements as described herein (e.g., direct displacement measurements of the neck or indirect measurements of the relative position of the neck suction device patient interface) as feedback. In some embodiments, force measurement may include an estimate of the force applied to the patient's neck using the intensity of the suction generated by treatment portion 103, the geometry of patient interface 115 (i.e., the surface area of the patient's neck to which suction is applied), and/or other factors. The present invention contemplates using any technique for measuring the force actually acting on the anatomical tissue of the user for use in the present invention.

In some embodiments, sensor portion 101 may be a displacement measurement device that is configured to measure or determine a displacement of a portion of a patient's anatomy. In some embodiments, the portion of the patient's anatomy where the displacement measurement is made or determined is the hyoid bone of the patient. Measurement of the displacement of the hyoid bone of the patient may be accomplished by measuring any given two elements of a neck suction treatment device (e.g., treatment portion 105). For example, a first position sensor may be attached to a patient interface 115 of treatment portion 105 that contacts the neck of the patient proximal to the hyoid bone of the patient. A second position sensor may be placed on a frame of system 100 (e.g., a housing for control portion 103, an outer portion of patient interface 115). If the second sensor is kept stationary, measurement of the difference in distance between these two position sensors over time can be used to determine the displacement of the first position sensor and thereby the displacement of the hyoid bone of the patient can be determined.

Figure 8:
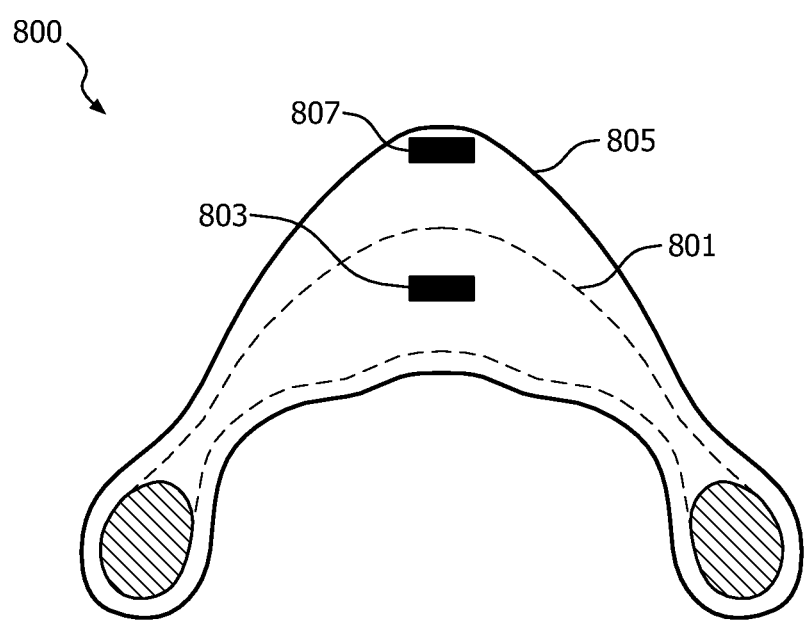
FIG. 8 illustrates an example of a patient engagement portion of a neck suction device, according to various embodiments of the invention.

FIG. 8 illustrates patient interface 800 having an inner, suction bladder portion 801 that is displaced when suction is applied to the neck of the patient. Suction bladder 801 may include a first sensor 803 that moves with suction bladder 801 when suction is applied to the neck of the patient. Patient interface 800 also includes an outer portion 805 that remains stationary when suction is applied to the neck of the patient. Outer portion 805 includes a second sensor 807 that also remains stationary when suction is applied to the neck of the patient. Accordingly, when suction is applied to the neck of the patient using patient interface 800, the difference in position between first sensor 803 and second sensor 807 may be used to arrive at a displacement of the hyoid bone of the patient, which may be used as described herein.

In some embodiments, the first position sensor may be attached directly to the neck of the patient rather (e.g., proximal to the hyoid bone of the patient) rather than on patient interface 115. Therefore, when suction is applied to the neck of the patient, the displacement of the surface of the neck itself may be used to determine the displacement of the hyoid bone of the patient.

A displacement measurement device that may be used as sensor portion 101 may include a position sensor or other motion sensing device. In some embodiments, position sensors used herein may include optical position sensors, inductive non-contact position sensors, string potentiometers, capacitive transducers, piezo-electric transducers, photodiode arrays, proximity sensors (e.g., Hall sensors), strain gauges, and/or other position sensing devices. In some embodiments, an optical sensor used herein may include a camera, a laser Doppler system, a proximity sensor, or other optical sensing equipment. In some embodiments, some or all position sensing equipment or other displacement measurement devices used as sensor portion 101 need not be attached to a patient. For example, a camera or other optical equipment may be trained on a patient interface or the surface of the neck of a patient to measure displacement.

In some embodiments, an optical marker tracking scheme may be used to measure displacement, wherein an optical sensing apparatus (e.g., a camera) may be used with optical markers other items (e.g., fiducials) attached to a patient interface, the neck of the patient, or other areas. In some embodiments, sensor portion 101 may include both a force and displacement measurement device. In some embodiments, two or more sensor devices may be used concurrently. The present invention contemplates using any technique for measuring the displacement of anatomical tissue for use in the present invention.

Control portion 103 may be or include a computer-implemented control device that includes one or more processing devices 107 (e.g., a microprocessors or micro-controllers), associated memory (not illustrated), input/output ports (not illustrated), and/or other features. Control portion 103 may include a control module 109, which may comprise computer-executable instructions that cause one or more processors 107 to perform the neck control therapy features and functions described herein such as, for example, receipt of patient secondary metric/characteristic information (e.g., hyoid force, hyoid displacement), control of a neck suction treatment device (e.g., treatment portion 105), and/or perform other calculations or determinations as described herein. Control module may include or may access memory storing one or more titration curves (or other titration information) or other information that is used to determine whether to increase or decrease suction intensity in light of measured metrics (e.g., force and/or displacement).

Control portion 103 may also include a user interface portion 117, which may include one or more items that may receive inputs from users and/or provide information to users. User interface portion 117 may include one or more buttons or touch screen elements as well as lights, textual display or other display elements. Various aspects of system 100 may be controlled using user interface portion such as, for example, power on/off, initial suction intensity, adjustment of intensity up/down, metric/characteristic measurement, and/or other functions.

In some embodiments, control portion 103 may also include a suction/vacuum generation device 111 that may enable treatment portion 105 to deliver suction to the exterior of a neck of a patient. For example, suction generation device 111 may include a blower, fan or other device that generates a negative pressure (suction), that is delivered, via conduit 113, to patient interface 115 of treatment portion 105 so as to deliver suction to the neck of the patient. Suction generation device 111 may be controlled by signals from one or more processors 107 such that the suction delivered to the patient's neck by treatment portion 105 may be adjusted up or down using the methods described herein or otherwise controlled.

Figure 7A:
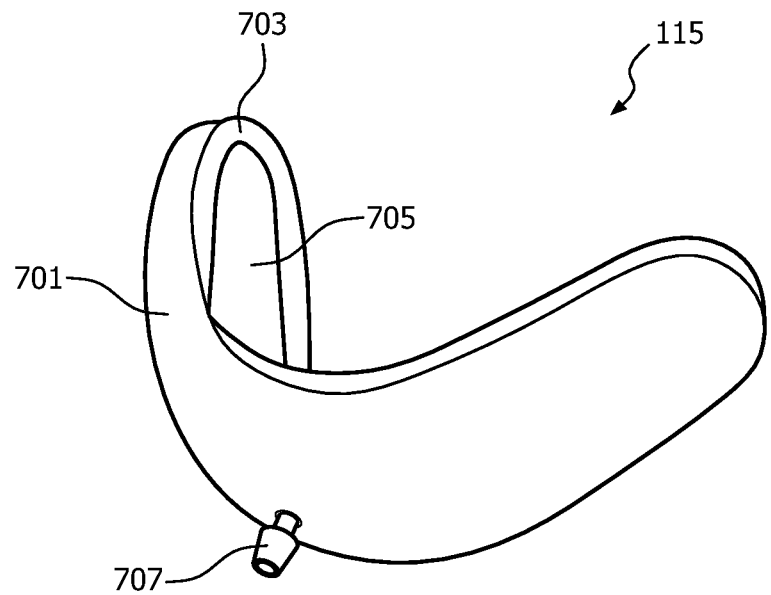
FIGS. 7A and 7B illustrate an example of a patient interface for a neck suction device, according to various embodiments of the invention.
Figure 7B:
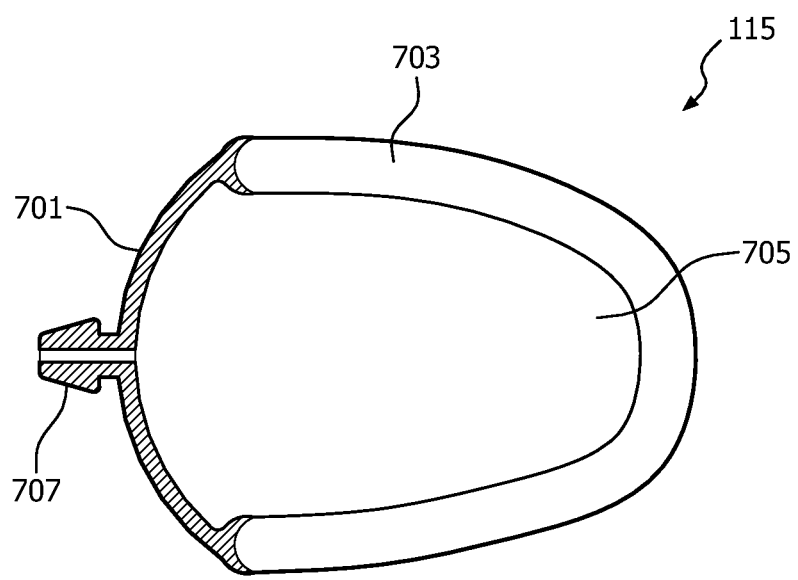

Treatment portion 105 may be or include a neck suction device that includes a conduit 113, a patient interface 115, and/or other items. Conduit 113 may be a flexible tube (e.g., rubber, plastic, polymer, etc.) that delivers suction generated by suction generation device 111 to patient interface 115. Patient interface 115 may be a flexible cup (e.g., rubber, plastic, polymer, etc.) or other applicator that engages the exterior of a patients body (e.g., the neck) to provide suction thereto. FIGS. 7A and 7B illustrate an example patient interface 115 (7B illustrating a cross section through the mid-plane of patient interface 115). Illustrated patient interface 115 may include a support wall 701, a sealing flap 703, an interior cup portion 705, and a vacuum attachment 707 (which attaches to conduit 113), and/or other features. As illustrated in FIGS. 2A and 2B, patient interface 115 may be positioned on the neck of the patient near the junction of the lower chin portion and the upper neck portion of the patient's neck (which is proximal to hyoid bone 205 of the patient). As described herein, the delivery of suction to the neck of a patient proximal to the hyoid bone may be useful in the treatment of obstructive sleep apnea (OSA) in that closures or obstructions in the patient's airway may be mitigated or prevented.

Treatment of OSA using neck suction can be improved by determining the precise amount of suction to apply to the neck so as to provide optimal symptom alleviation. Accordingly, the suction intensity or negative pressure applied to the surface of the patient's neck can be titrated so that the maximum effectiveness of the treatment can be achieved with minimum irritation or disturbance to the patient. Such titration is possible when primary metrics such as, for example blood oxygenation, respiratory airflow, or other primary metrics that can be directly measured. However, measurement of such primary metrics can involve complex and invasive sensors. Accordingly, provided herein are systems and methods for using one or more secondary metrics to control a neck suction device.

Figure 3:
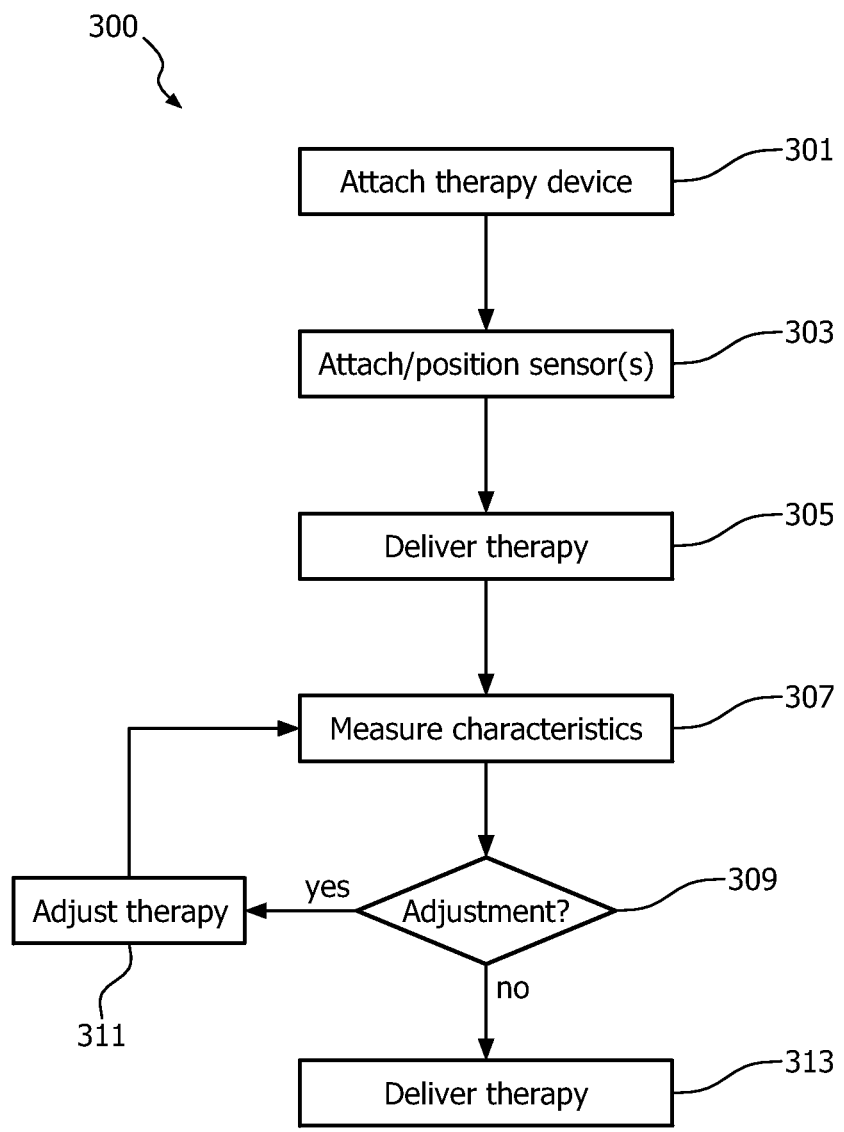
FIG. 3 is an example of a process for control of a neck suction device using secondary metrics according to various embodiments of the invention.

FIG. 3 illustrates a process 300, which is an example of a process for using secondary metrics to control a neck suction device (e.g., using system 100 of FIG. 1). Process 300 may include an operation 301, wherein a therapy device is attached to a patient. For example, patient interface 115 of treatment portion 105 of system 100 may be attached to a patient. As described herein, treatment portion 105 may include a neck suction device. FIGS. 2A and 2B illustrate that patient interface 115 may be located at or near the exterior surface of the patient's neck proximal to the hyoid bone 205 (e.g., patient interface 115 may be placed at or near the junction of the lower chin portion and upper neck portion of the patient's throat). In some embodiments, the suction provided by the neck suction device may serve to sufficiently affix patient interface 115 to the neck of the patient. Accordingly, in some instances a patient interface may be held in place by a patient or other person prior to commencement of suction delivery. In some embodiments, a patient interface may be (at least initially) held in place via straps around the neck of the patient or other attachment elements.

In an operation 303, one or more sensors may be attached to the patient or otherwise positioned to obtain information regarding one or more characteristics of the anatomy of the patient (i.e., secondary metrics). For example, in some embodiments, sensor portion 101 of system 100 maybe affixed to patient interface 115, to the neck of the patient, or otherwise positioned to measure one or more characteristics. In some embodiments, an optical sensor may be positioned so as to measure displacement of the surface of the patient's neck proximal to the hyoid bone. As described herein, in some embodiments, the sensor portion may include sensors that measure force measurement and/or displacement. The present invention further contemplates using secondary metrics alone or in combination with a primary metric measurement, such as the intensity of the vacuum or pressure within the vacuum chamber, to control the vacuum applied to the user.

In some embodiments, the sensor may be attached to the patient interface or the patient using adhesive. In some embodiments, other attachment methods may also be used and/or the portions of sensors need not be directly attached to the patient but may be otherwise positioned (e.g., a camera for optical sensing schemes may be pointed at the patient interface or patient's neck). FIGS. 2A and 2B illustrate that sensors 101 may be placed on patient interface 115 of a neck suction device (which is placed near the junction of the lower chin portion and the upper neck portion of the patient's throat). Other sensor placements may be used.

In an operation 305, the neck suction device may be used to deliver suction therapy to the neck of the patient at an initial intensity. In some embodiments, the intensity of suction delivered to the neck of the patient may be measured using centimeters of water (cmH$_2$O). In some embodiments, the initial intensity may be a predetermined intensity (e.g., between 0 to 100 cmH$_2$O) that is delivered upon startup.

In an operation 307, one or more characteristics (i.e., secondary metrics) of the of the anatomy of the patient (e.g., the neck) are measured/determined. For example, when a sensor portion 101 that is a force measurement device is used, the force applied to the hyoid bone of the patient by the neck suction device may be measured/determined. When a sensor portion 101 that is a displacement measurement device is used, the displacement of the hyoid bone of the patient effected by the neck suction device may be measured/determined. As described herein, in some embodiments, both the force applied to the hyoid bone and the displacement of the hyoid bone may be measured/determined.

Figure 6:
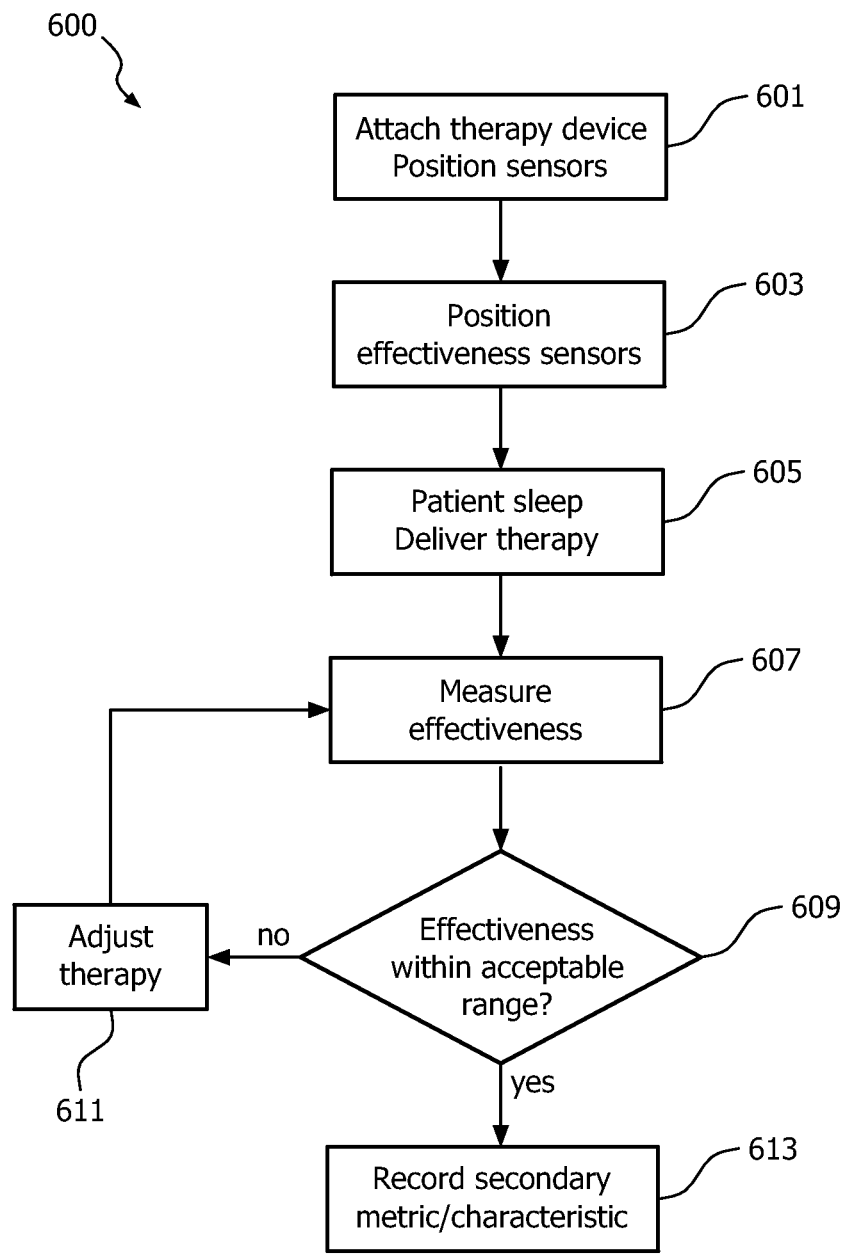
FIG. 6 is an example of a process for titrating neck suction therapy delivery to a patient, according to various embodiments of the invention.

In an operation 309, the characteristic measurement(s) may be used to determine whether the suction intensity delivered to the patient's neck should be adjusted. In some embodiments, this may be done by comparing the measured force and/or displacement values to a titration curve. In some embodiments, the titration curve may be a plot of one or more primary metrics relating to the effectiveness of neck suction therapy (such as, for example, SpO2 (blood oxygenation), respiratory effort, heart rate, subclavian notch motion, or airflow of breathing) against hyoid displacement or force metrics. In some embodiments, the desired or optimal values for a secondary metrics/characteristic values that provide optimal treatment may be known from a titration procedure for the patient. FIG. 6. illustrates a process 600 which is an example of a titration procedure used with a patient so as to determine an optimal secondary metric value for providing neck suction therapy.

Process 600 includes an operation 601, wherein a neck suction device (e.g., treatment portion 105) is attached to the patient and one or more sensors for measuring one or more secondary metrics (e.g., sensors 101) are positioned so as to measure such secondary metrics of the patient. In an operation 603, one or more devices for measuring the effectiveness of the treatment delivered to the patient (i.e., primary metrics) are positioned. For example, a flow sensor may be placed in communication with a patient's airway so as to measure airflow through the patient's respiratory system. This measurement may be a primary metric for the effectiveness of respiratory therapy for OSA.

In an operation 605, the patient is allowed to fall asleep and therapy (i.e., neck suction) is delivered to the patient. In an operation 607, the flow sensor or other device for measuring the effectiveness of the delivered therapy measures the primary metric. For example, the respiratory flow sensor described herein may monitor for sleep apnea/Hypopnea events. In an operation 609 it may be determined whether the primary metric indicates that the treatment is effective (e.g., that an apnea Hypopnea index (AHI) is within a clinically acceptable range (e.g., less than 5)). If it is determined that the treatment is not effective, (e.g., the AHI is not within a clinically acceptable range), the therapy delivered to the patient may be adjusted (e.g., suction increased) in an operation 611. Process 600 may then return to operation 607, wherein the treatment effectiveness (or indicators thereof) is measured.

If, in operation 609, it is determined that the treatment is effective (e.g., AHI is within a clinically acceptable range), a secondary characteristic measurement (e.g., force or displacement measurement) is taken and saved for use in future treatment sessions (e.g., for operation 309 of process 300).

Returning to process 300, if, in operation 309, it is determined that the measured displacement or force is found not be at a desired level, the intensity of the neck suction delivered to the patient may be adjusted accordingly in an operation 311. For example, if the force applied to the patient's hyoid bone is thought to be too large, while the airway of the patient may be opened (and thus effective therapy may be delivered), the neck suction device may be unnecessarily irritating the patient's skin or neck. Delivering such therapy with too much force may lead to decreased patient compliance. Accordingly, if the force is determined to be too large, the neck suction intensity may be decreased. This may be implemented by control portion 103 causing suction generation device 111 to decrease the generated suction delivered to the patient.

In another example, if the force applied to the patient's hyoid bone is too low, then the airway may not be effectively opened. Accordingly, the neck suction intensity may be increased (e.g., control portion 103 causing suction generation device 111 to increase the intensity of the section delivered to the patient).

In another example, if the displacement of the patient's hyoid bone is too low, the neck suction treatment may not be effective (e.g., the airway may not be opened by a suitable amount). Accordingly the intensity of the neck suction may be increased (e.g., control portion 103 may cause suction generation device 111 to increase the suction delivered to the neck of the patient). Conversely, if the hyoid displacement of the patient is measured to be too great, the suction delivered to the patient may be to intense and may be causing discomfort or irritation (which may affect patient compliance). Accordingly the neck suction may be decreased (e.g., by control portion 103 causing suction generation device 111 to lower the suction delivered to the patient).

After an adjustment to the delivered therapy is made in operation 311, process 300 may return to operation 307, wherein the one or more secondary metrics/characteristics are measured again. A new determination may then be made in operation 309 as to whether further adjustment must be made.

If, in operation 309 is it determined that the neck suction is not to be adjusted (i.e., the secondary metric(s) are at desired levels), then process 300 proceeds to an operation 313 wherein therapy is delivered until such time as the patient or another user ends therapy delivery.

In the manner described with respect to process 300, an optimal suction intensity may be reached for neck suction therapy. As the optimal suction intensity may vary from person to person and according to other factors (e.g., the position of the patient, the geometry of a patient interface, etc.) such on-site secondary metrics provide more effective and personalized neck suction therapy. Furthermore, the use of sensors for measuring primary effectiveness metrics can be avoided. The final criteria for effectiveness of therapy may be the elimination of symptoms (e.g., daytime sleepiness for OSA sufferers). However, the use of secondary metrics described herein (which are linked to specific physiologic parameters (e.g., $O_2$ saturation, respiratory arousals, AHI index, or other parameters) enables a determination of the minimum suction/force for delivery to the patient so as to effectively stabilize the patients airway to eliminate such symptoms (e.g., daytime sleepiness).

As discussed above, some patients do not receive effective treatment from neck suction therapy due to their individual anatomical variations. For example, the specific anatomy of some patients may be such that neck therapy may not be an effective method of treatment for OSA. The tissue of the neck may be too stiff or heavy such that neck suction may not effect hyoid bone displacement enough to increase respiratory airflow. Conversely, the outer tissue of the neck may be too pliable (e.g., flabby) such that neck suction applied to external portions of the neck proximal to the hyoid bone will not translate into displacement of the hyoid bone enough to increase respiratory airflow. Accordingly, the same secondary metrics used for optimization of neck suction intensity may be used as a screening tool to identify candidates for which the vacuum therapy has a high likelihood of successfully opening the airway. Therefore, in some embodiments, the systems and methods described herein may provide for evaluation of the effectiveness of neck suction therapy for a patient.

Figure 4:
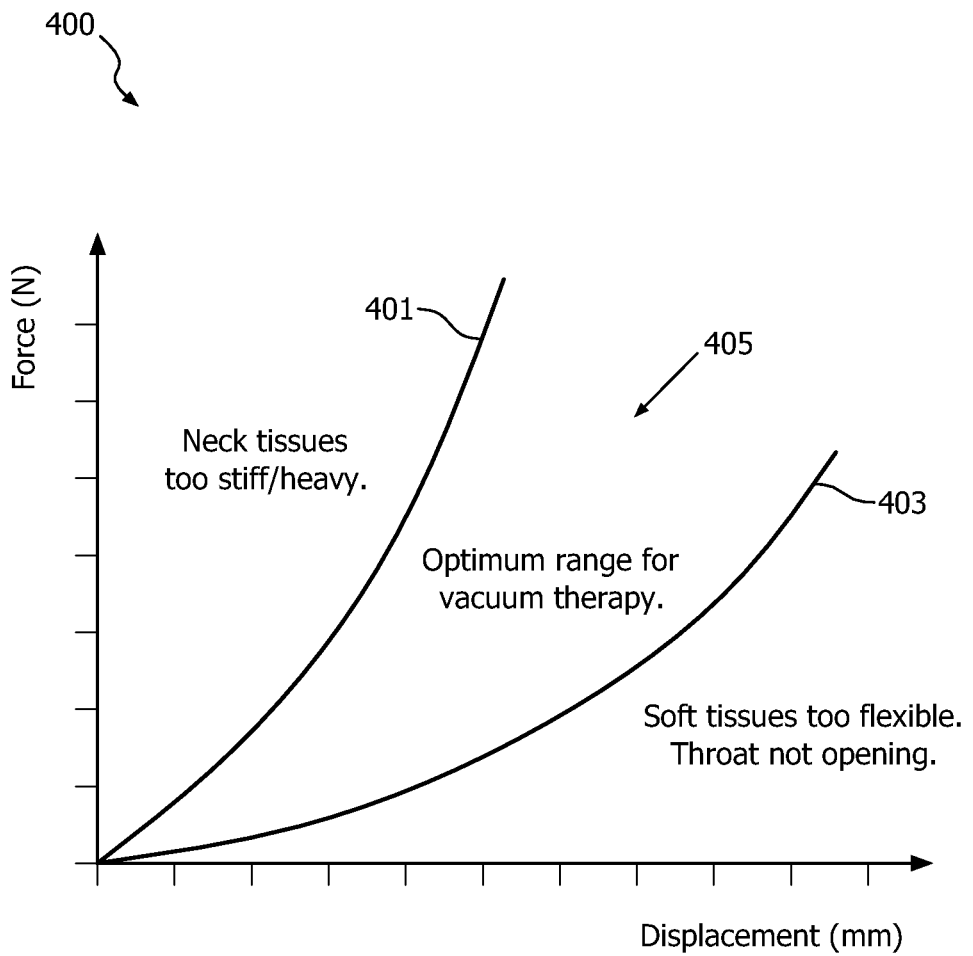
FIG. 4 is an example of a graph illustrating an optimal range for patient responsiveness to neck suction treatment, according to various embodiments of the invention.

FIG. 4. provides a graph 400 which includes example force/displacement curves that illustrate the principle that an optimal patient anatomy exists for receiving neck suction treatment. Curves 401 and 403 illustrate that an optimal range, shown as area 405, exists for patient responsiveness to neck suction therapy.

Figure 5:
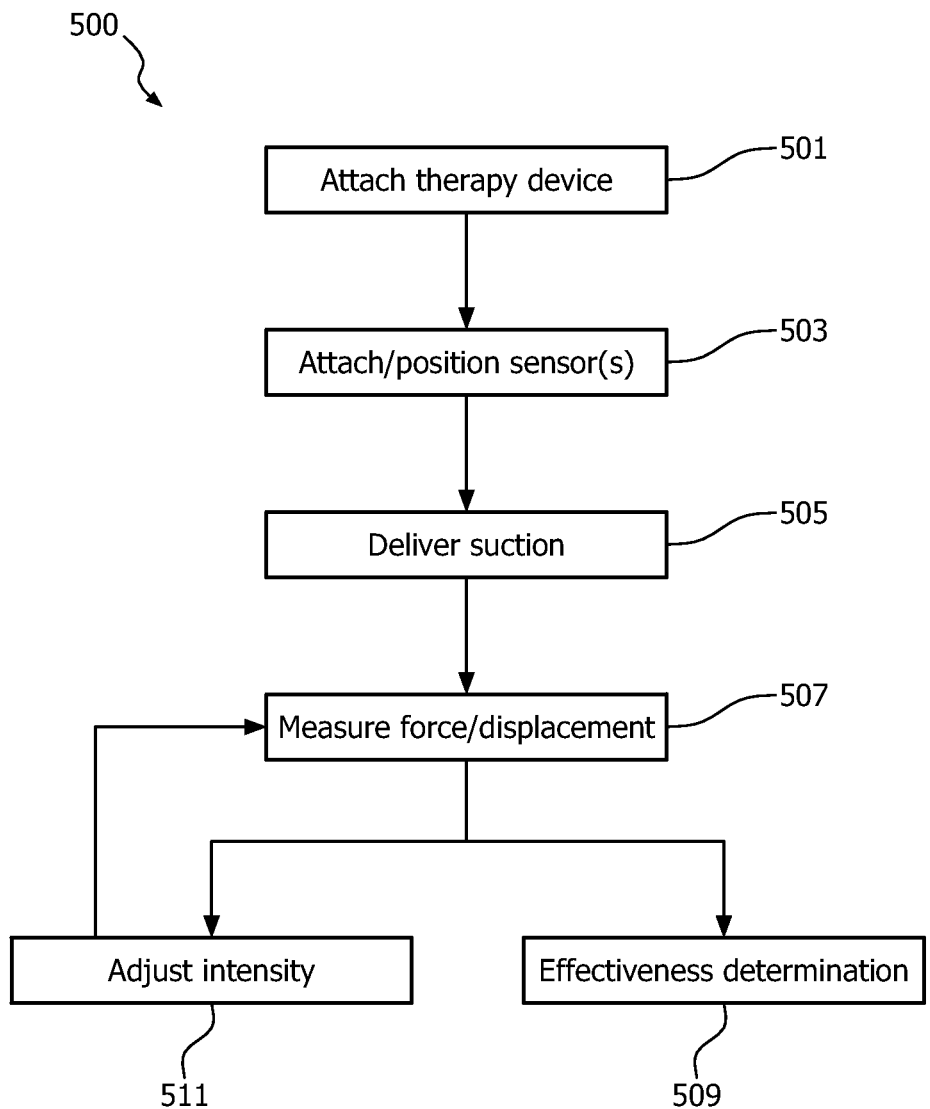
FIG. 5 is an example of a process for determining patient responsiveness to neck suction, according to various embodiments of the invention.

FIG. 5 illustrates a process 500, which is an example of a process for using secondary metrics to evaluate whether a neck suction device can provide effective therapy. In an operation 501, a neck suction device (e.g., e.g., treatment device 101) is attached to a patient. In an operation 503, one or more sensors for measuring one or more of force applied by the neck suction device to the hyoid bone of the patient or displacement of the hyoid bone of the patient may be attached to the patient or otherwise positioned so as to obtain such measurements. In some embodiments, only a displacement sensor may be used as the force applied by a given suction intensity of the neck suction device may be estimated using the suction intensity, patient interface geometry, and/or other factors.

In an operation 505, the neck suction device may be used to deliver suction to the neck of the patient at an initial intensity. In some embodiments, the initial intensity may be a low intensity such that the intensity and therefore the force applied to the patient can be increased for purposes of producing the desired force/displacement curve. In some embodiments, a high intensity may be used and the intensity may be lowered to derive the desired measurements. In an operation 507, the force resulting from the initial intensity may be measured and/or the displacement of the hyoid bone resulting from such force. In some embodiments, the displacement caused by the initial applied suction or force is used, in an operation 509, to determine whether neck suction therapy is likely to be an effective therapy. This may be accomplished by comparing the displacement effected by the delivered suction or force to a lookup table or curve (e.g., curve 400) that indicates whether the patient's responsiveness to suction/force places the patient in a treatable range. The effectiveness determination may be performed automatically by a computer-implemented device such as, for example control portion 103 of system 100 or may be performed by a technician or other person.

In some embodiments, additional data relating to the responsiveness of the patient to delivered suction/force may be needed or desired. Accordingly, in an operation 511, the intensity of suction applied to the patient's neck is adjusted up or down according to the starting intensity (e.g., control portion 103 causes suction generation device 111 to increase or decrease the suction delivered to the patient's neck). Process 500 may then return to operation 507, wherein the corresponding force applied to the patient's neck and resulting displacement may be measured (e.g., using sensors 101). Process 500 then returns to operation 509, wherein it may be determined whether neck suction therapy is likely to be effective. This process may continue through cycles of adjustment and measurement until an effectiveness prediction/determination can be made.

Embodiments described in this disclosure may be made in hardware, firmware, middleware, software, or various combinations thereof. Computer-readable instructions stored on a tangible, non-transitory computer-readable storage medium for performing the features and functions described herein may be provided. The computer-readable instructions may be read and executed by one or more processors may cause the one or more processors to perform the features and functions of the systems and processes described herein. A computer-readable storage medium may include various mechanisms for storing information in a form readable by a computing device. For example, a tangible computer-readable storage medium may include optical storage media, flash memory devices, and/or other storage mediums. Further, firmware, software, routines, or instructions may be described in the above disclosure in terms of specific exemplary aspects and implementations of the technology, and performing certain actions. However, it will be apparent that such descriptions are merely for convenience, and that such actions may in fact result from computing devices, processors, controllers, or other devices executing firmware, software, routines or instructions.

The systems described herein are exemplary system configurations. Other configurations may exist. Those having skill in the art will appreciate that the invention described herein may work with various configurations. Accordingly, more or less of the aforementioned system components may be used and/or combined in various embodiments. Furthermore, various operations of the methods described herein, while described in a particular order, may be performed in different orders as would be appreciated by those having skill in the art. In some embodiments, more of less of the described operations may be used.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for providing neck suction therapy, comprising:
    a neck suction portion, the neck suction portion comprising a patient interface configured to engage and apply suction to an area on a neck of a patient proximal to a hyoid bone of the patient;
    a sensor portion configured to measure one or more characteristics of the area on the neck of the patient during application of suction by the neck suction portion, the one or more characteristics comprising a displacement of the hyoid bone of the patient caused by application of suction by the neck suction portion; and
    one or more processors configured to:
        receive information regarding the measured displacement of the hyoid bone of the patient caused by application of suction; and
        adjust a suction intensity of the neck suction portion based on the measured displacement of the hyoid bone of the patient caused by application of suction.

2. The system of claim 1, wherein the measured one or more characteristics comprise a force applied to the hyoid bone of the patient by the neck suction portion.

3. The system of claim 2, wherein at least a portion of the sensor portion is physically attached to one or more of the area on the neck of the patient or a portion of the patient interface of the neck suction portion.

4. The system of claim 1, wherein the sensor portion is an optical sensor positioned to optically capture displacement of the hyoid bone on the neck of the patient.

5. The system of claim 1, wherein the one or more processors is configured to:
    compare the received measured displacement of the hyoid bone of the patient caused by application of suction to a predetermined displacement value; and
    adjust the suction intensity based on the comparison.

6. A system for controlling a neck suction device, comprising:
    treatment means for applying suction to an area on a neck of a patient proximal to a hyoid bone of the patient;
    sensor means for measuring one or more characteristics of the area on the neck of the patient during application of suction by the treatment means, the one or more characteristics comprising a displacement of the hyoid bone of the patient caused by application of suction by the neck treatment means; and
    processor means for:
        receiving information regarding the measured displacement of the hyoid bone of the patient caused by application of suction; and
        adjusting a suction intensity of the treatment means based on the measured displacement of the hyoid bone of the patient caused by application of suction.

7. The system of claim 6, wherein the measured one or more characteristics comprise a force applied to the hyoid bone of the patient by the treatment means.

8. The system of claim 6, wherein at least a portion of the sensor means is physically attached to one or more of the area on the neck of the patient or a portion of a patent interface of the neck suction device.

9. The system of claim 6, wherein the sensor means is an optical sensor positioned to optically capture displacement of the hyoid bone of the patient caused by application of suction.

10. The system of claim 6, wherein the processor means further comprises processor means for:
    comparing the received measured displacement of the hyoid bone of the patient caused by application of suction to a predetermined displacement value, and
    adjusting the suction intensity based on the comparison.

* * * * *